United States Patent [19]

Walsh

[11] Patent Number: 4,855,448

[45] Date of Patent: Aug. 8, 1989

[54] 2-AMINO-3-AROYL-γ-OXOBEN-ZENEBUTANOIC ACIDS AND ESTERS

[75] Inventor: David A. Walsh, Richmond, Va.

[73] Assignee: A. H. Robins Company, Incorporated, Richmond, Va.

[21] Appl. No.: 229,665

[22] Filed: Aug. 8, 1988

Related U.S. Application Data

[62] Division of Ser. No. 900,599, Aug. 26, 1986, Pat. No. 4,782,089.

[51] Int. Cl.$^4$ .................. C07D 403/06; C07D 209/16
[52] U.S. Cl. .................. 548/504; 546/201; 544/143
[58] Field of Search ............ 548/504; 544/143; 546/201

[56] References Cited

U.S. PATENT DOCUMENTS 2,890,223  6/1959  Wooley et al. ............ 548/494 X

*Primary Examiner*—David B. Springer

[57] ABSTRACT

2-Amino-3-aroyl-γ-oxobenzenebutanoic acids and derivatives having the formula:

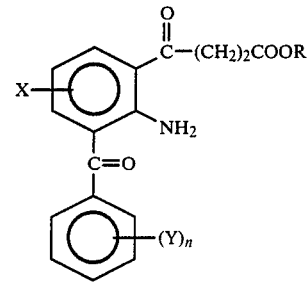

wherein X is hydrogen, halogen, or loweralkyl; Y is hydrogen, halogen, loweralkyl, loweralkoxy, nitro, or trifluoromethyl; n is 1 or 2; and R is hydrogen, loweralkyl, or a pharmaceutically acceptable cation, are disclosed having anti-inflammatory activity.

3 Claims, No Drawings

2-AMINO-3-AROYL-γ-OXOBENZENEBUTANOIC ACIDS AND ESTERS

This is a division of application Ser. No. 900,599, filed 8/26/86, now U.S. Pat. No. 4,782,089.

BACKGROUND OF THE INVENTION

1. Field of Invention

The present invention relates to novel 2-amino-3-aroyl-γ-oxobenzenebutanoic acids, novel methods of preparation thereof, novel intermediates therefor, and pharmaceutical methods and compositions for treating living animals for pain and inflammation therewith.

2. Description of the Prior Art

2-Amino-3-aroyl-benzeneacetic acids, esters, and metal salts thereof have been disclosed as having anti-inflammatory activity in U.S. Pat. No. 4,045,576 and as having anti-inflammatory and analgesic activity by Sancilio, L. F. et al. in Agents and Actions, Vol. 7/1 (1977) Birkauser Verlag Basel Schweiz. These compounds do not have a keto group on the alkanoic acid chain.

3-Aroyl-γ-oxobenzenebutanoic acids have been disclosed in U.S. Pat. No. 3,784,701 as having anti-inflammatory and analgesic activity. These compounds do not have a 2-amino group on the primary benzene ring as do the compounds of the present invention.

SUMMARY OF THE INVENTION

The novel 2-amino-3-aroyl-γ-oxobenzenebutanoic acids of this invention have the formula:

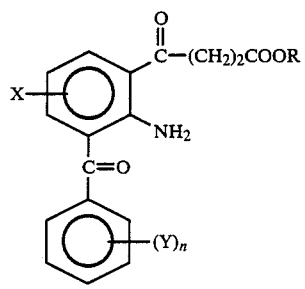

wherein X is selected from hydrogen, halogen, or loweralkyl; Y is selected from hydrogen, halogen, loweralkyl, loweralkoxy, nitro, or trifluoromethyl; n is 1 or 2; R is H, loweralkyl, or a pharmaceutically acceptable cation.

In the further definition of symbols and in the formulas hereof and where they appear elsewhere throughout this specification and in the claims, the terms have the following significance.

The term "loweralkyl" as used herein, unless otherwise specified, includes straight and branched chain radicals of up to eight carbons inclusive and is exemplified by such groups as methyl, ethyl, propyl, isopropyl, butyl, sec.butyl, tert.butyl, amyl, isoamyl, hexyl, heptyl, and octyl radicals, and the like. The term "loweralkoxy" has the formula —O—loweralkyl.

The terms "halo" or "halogen" as used herein includes fluorine, chlorine, bromine, and iodine. Preferably, the halogen is chlorine or bromine.

The term "pharmaceutically acceptable cation" includes cations selected from such as sodium, potassium, calcium, magnesium, zinc, aluminum, copper, and the hydrates of the salts formed therewith when they occur.

The compounds of the present invention are useful in controlling inflammation and pain and in inhibiting blood platelet aggregation.

The anti-inflammatory utility of the novel compounds of this invention was determined using a modification of the Evans Blue-Carrageenan Pleural Effusion Assay of Sancilio, L. F., J. PHARMACOL. EXP. THER. 168, 199–204 (1969), and a modification of the Adjuvant-Induced Arthritis Method of Walz, D. T. et al., J. PHARMAC. EXP. THER. 178, 223–231 (1971). See Pharmacology hereinbelow for description of tests.

The analgesic utility of the compounds of Formula I was determined by a modification of the method of Collier et al., J. BR. PHARMAC. CHEMOTHER. 32, 295–310 (1968). (See Pharmacology hereinbelow for description of test).

Novel intermediates used in the preparation of compounds of Formula I are the compounds of Formulas II, III and IV below:

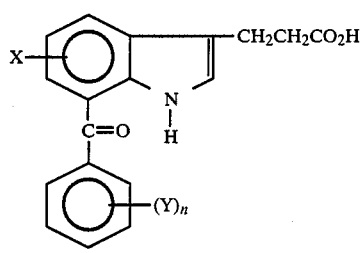

Formula II

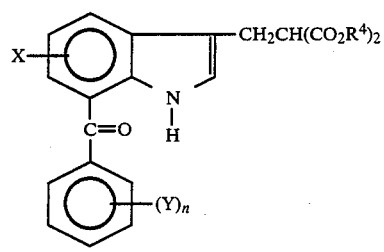

Formula III

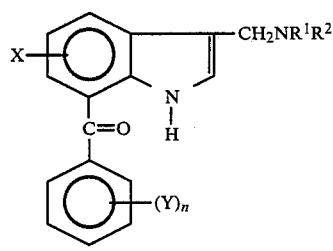

Formula IV wherein X and Y are as defined under Formula I; $R^1$ and $R^2$ are selected from loweralkyl or, when taken together with the adjacent nitrogen atom, may form a heterocyclic amine selected from 1-pyrrolidinyl, 1-piperidinyl or 4-morpholinyl; and $R^4$ is selected from hydrogen, loweralkyl or a metal cation selected from sodium, potassium, barium or calcium.

The compounds of Formula I are pharmacologically active anti-inflammatory analgesic prodrugs of 2-amino-3-benzoyl-benzeneacetic acids described in U.S. Pat. No. 4,045,576 and as such are capable of providing effectiveness in controlling inflammation and pain in living animals at a later time interval than the benzeneacetic acids. The effectiveness as an anti-inflammatory and analgesic of 3-benzoyl-benzeneactiic acid (AHR- 5850) is described by Sancilio, L. F. et al. in Agents and Actions (See reference above).

It is therefore an object of the present invention to provide novel compounds via novel intermediates and compositions useful in the control of inflammation, pain, and blood-platelet aggregation.

A further object is to provide prodrugs which break down to the 2-amino-3-benzoyl-benzeneacetic acids after administration to living animals which are primarily responsible for the pharmacological activity, thus providing a more gradual and longer lasting effect than would be obtained from administration of the 2-amino-3-benzoyl-benzeneacetic acids.

Additional objects will be apparent to one skilled in the art and still other objects will be apparent hereinafter.

DETAILED DESCRIPTION OF THE INVENTION

The compounds of Formula I are prepared by reactions represented by equations given in Chart I.

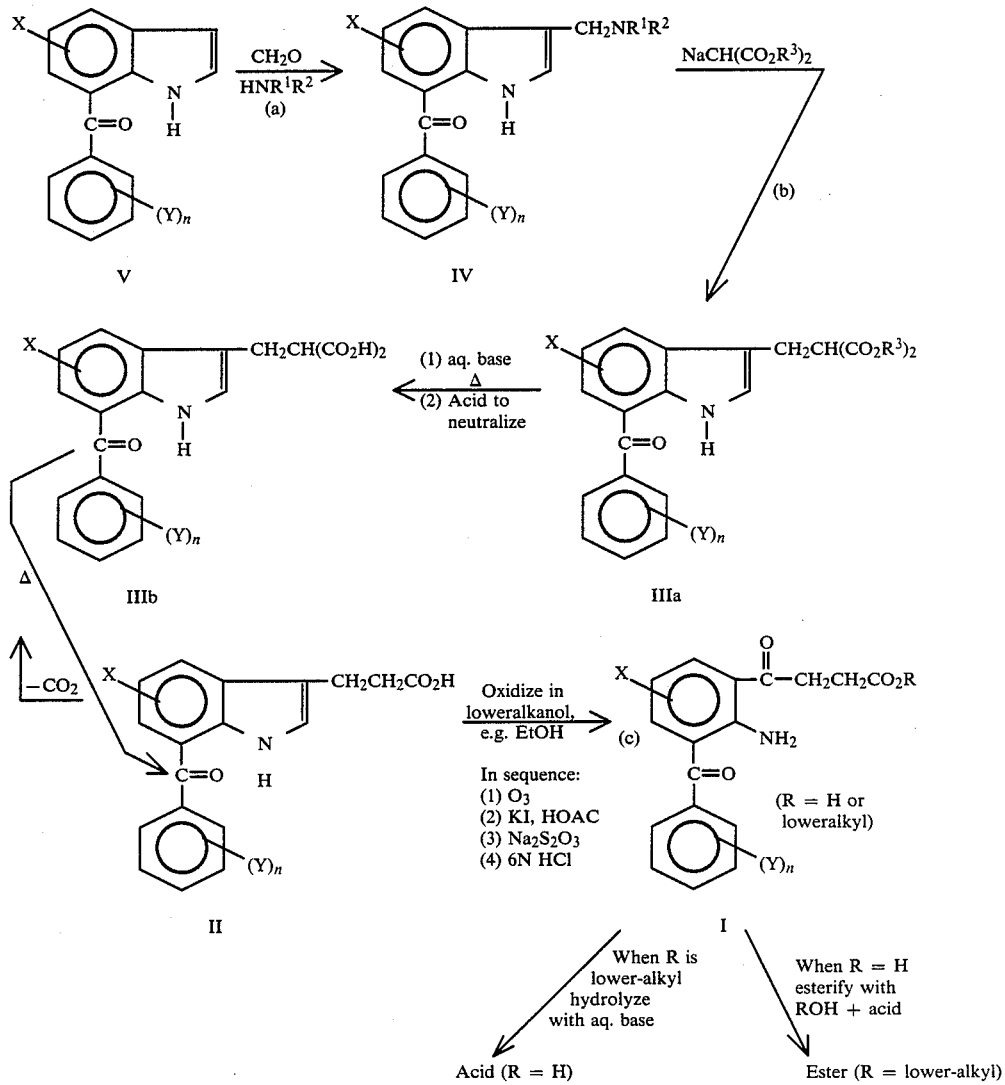

Footnotes to Chart I:

(a) Any secondary $HNR^1R^2$ amine is satisfactory such as wherein $R^1$ and $R^2$ = loweralkyl or form a heterocyclic such as 1-pyrrolidinyl, 1-piperidinyl or 4-morpholinyl.

(b) Any sodiomalonate wherein $R^3$ forms an ester may be used, such as $R^3$ = loweralkyl.

(c) More concentrated alcoholic solution tends to give ester rather than acid.

The 2-amino-3-aroyl-γ-oxobenzenebutanoic acids and esters are prepared by a novel method comprising the following sequence of steps:

Step 1, reacting an indole having the formula:

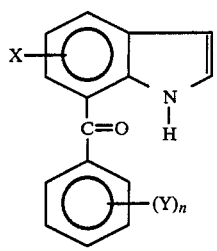

wherein X, Y and n are as defined under Formula I with formaldehyde and an amine having the formula:

wherein $R^1$ and $R^2$ are selected from loweralkyl or when taken together with the nitrogen atom, may form a heterocyclic amine such as 1-pyrrolidinyl, 1-piperidinyl or 4-morpholinyl to give a compound having the formula:

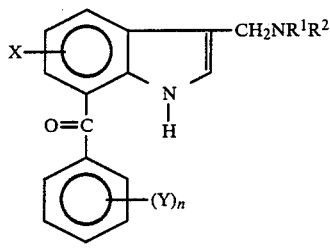

wherein X, Y, n, $R^1$ and $R^2$ have the starting values,

Step 2, reacting the compound prepared in Step 1 with an alkali-metal salt of a diloweralkyl ester of malonic acid having the formula:

MCH(COOR³)₂ wherein M is an alkali-metal and $R^3$ is loweralkyl to give a compound having the formula:

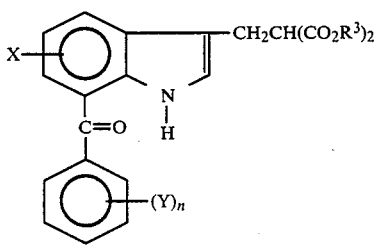

wherein X, Y, n and $R^3$ have the values assigned above,

Step 3, de-esterifying a compound prepared in Step 2 by heating it in aqueous basic solution and thereafter adding acid to give a compound of the formula:

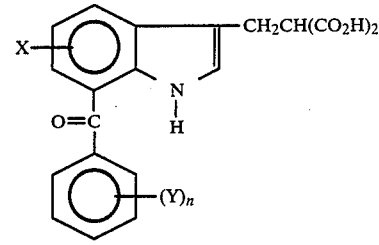

wherein X, Y, and n have the values assigned above,

Step 4, decarboxylating a compound prepared in Step 3 by heating to liberate carbon dioxide to give a compound having the formula:

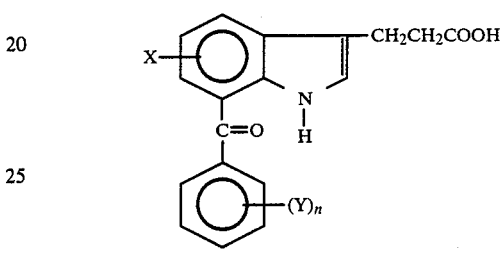

wherein X, Y and n have the values assigned above,

Step 5, oxidizing a compound prepared in Step 4 with ozone to give a compound having the formula:

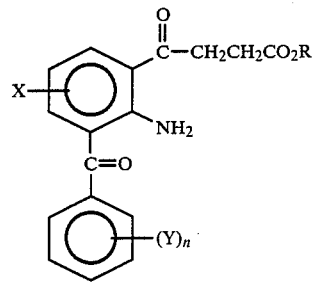

wherein R is hydrogen or loweralkyl and X, Y, and n have the values assigned above and thereafter decomposing excess ozone, Step 6, esterifying a compound prepared in Step 5 with a loweralkanol wherein R is H to give a compound wherein R is loweralkyl Step 7, de-esterifying a compound prepared in Step 5 wherein R is loweralkyl by hydrolysis in aqueous base and neutralizing with a strong acid.

In reference to the process steps summarized above as they apply to the preparation of compounds of Formulas I, II, III, and IV, the following further description is applicable:

In Step 1, illustrated by the preparation of Intermediates 1 and 5, an aqueous solution of the $HNR^1R^2$ amine and formaldehyde solution are reacted in the cold ca. 0°–10° C. and added to a mixture of the 7-benzoyl-1H-indole in acetic acid. Ethanol is added to the mixture which is then warmed. The preferred amine is dimethylamine as any excess amine is easily evaporated off.

The product is separated by partitioning into the organic phase of a mixture of aqueous base and a solvent such as methylene chloride and evaporating the solvent and recrystallizing.

In Step 2, illustrated by the preparation of Intermediates 2 and 6, the 3-aminoalkyl-indolo-phenylmethanone is reacted with diloweralkyl alkali-metal malonate formed, for example, by sodium hydride and diloweralkyl malonate ester by refluxing in an aprotic solvent such as xylene until reaction has occurred. The product is isolated by conventional means such as evaporation of solvent and recrystallizing or by high pressure liquid chromatography.

In Step 3, illustrated by the preparation of Intermediates 3 and 7, the propanedioic acid ethyl ester derivative is heated in intermediate strength base such as 3N sodium hydroxide. Other bases (MOH) which are suitable are those such as potassium, calcium, and barium hydroxides. At this point the liberated propanedioic acid is in the form of its metal salt corresponding to the base used. A strong acid such as hydrochloric acid is added to give the free propanedioic acid derivative and the product is separated by conventional precipitation and filtration.

In Step 4, illustrated by the preparation of Intermediates 4 and 8, the propanedioic acid derivative is heated at about 180°–210° C. under reduced pressure until liberation of carbon dioxide ceases. The product is obtained by cooling the resulting melt.

In Step 5, illustrated by Examples 1 and 2, the propanoic acid derivative is oxidized with ozone in a mixture of ethanol and ethyl acetate. Aqueous potassium iodide is added. Liberated iodine is removed by washing with sodium thiosulfate solution and the organic layer is concentrated. The residue is dissolved in a suitable solvent; e.g., ethanol, and heated with 6N hydrochloric acid under reflux. The solution is again concentrated and the residue is partitioned between dilute aqueous base and methylene chloride and the product is isolated by conventional means. In this step, the more concentrated the initial solution is, the more likely an ester will result.

Steps 6 and 7 are conventional esterification and de-esterification steps which are employed depending on whether an acid is obtained in Step 5 and an ester is desired or whether an ester is obtained in Step 5 and an acid is desired.

Metal salts of acids obtained in Steps 5 or 7 may be obtained by conventional means.

The procedure for the synthesis of the starting indole derivatives is as disclosed in U.S. Pat. No. 4,221,716. The route is indolines→7-benzoylindolines→7-benzoylindoles.

The following Intermediates 1–8 illustrate the synthesis of compounds of Formulas II, III, and IV, and the following Examples 1–3 illustrate the synthesis of compounds of Formula I and should in no way be regarded as limiting, the limiting factors being only the definitions given under Formulas I, II, III, and IV. Variations in X and Y are brought about by starting with the appropriate corresponding indole as would be recognizable by one skilled in the art.

INTERMEDIATE 1

[3-[(Dimethylamino)methyl]-1H-indol-7-yl]phenylmethanone

An 18.0 g (0.16 mole) portion of 40% aqueous dimethylamine was cooled to 5° C. and 24 g (0.4 mole) of glacial acetic acid was added. To this mixture, held at 5° C., was added 12.2 g (0.15 mole) of 37% formalin. This aqueous mixture was added to a mixture of 33.1 g (0.15 mole) of 7-benzoyl-1H-indole and 20 ml of acetic acid. After 100 ml of absolute ethanol was added to the mixture, it was warmed on a steam bath for ½ hr. Isolation of the product was accomplished by concentrating the mixture under reduced pressure, partitioning between dilute sodium hydroxide and methylene chloride and concentrating the organic solution. The residue was recrystallized from isopropyl alcohol to give 29 g (70%) of light yellow crystals, m.p. 111.0°–113.5° C.

Analysis: Calculated for $C_{18}H_{18}N_2O$: C, 77.67; H, 6.52; N, 10.06. Found: C, 78.07; H, 6.49; N, 10.07.

INTERMEDIATE 2

2-[(7-Benzoyl-1H-indol-3-yl)methyl]propanedioic acid, diethyl ester

A mixture of 19.4 g (0.07 mole) of [3-[(dimethylamino)methyl]-1H-indol-7-yl]phenylmethanone and 32.5 g (0.2 mole) of diethyl sodiomalonate prepared from 0.85 g (0.2 mole) of 57% sodium hydride in oil and 32 g (0.2 mole) of diethyl malonate in 50 ml of xylene was heated at reflux for 17 hr. The mixture was cooled, diluted with diethyl ether and washed with water. The solvent and excess reagents were removed by distillation at high vacuum. The residue was crystallized first from isopropyl alcohol and then from isopropyl ether to give 12.6 g (46%) of light yellow powder, m.p. 86.0°–88.0° C.

Analysis: Calculated for $C_{23}H_{23}NO_5$: C, 70.22; H, 5.89; N, 3.56. Found: C, 70.50; H, 5.93; N, 3.61.

INTERMEDIATE 3

2-[(7-Benzoyl-1H-indol-3-yl)methyl]propanedioic acid

A mixture of 10.0 g (0.025 mole) of 2-[(7-benzoyl-1H-indol-3-yl)methyl]propanedioic acid diethyl ester in 150 ml of 3N sodium hydroxide was heated at reflux for 18 hr, then treated with charcoal, cooled and filtered. The dark yellow filtrate was acidified by the dropwise addition of 50 ml of concentrated hydrochloric acid. The addition of 20 ml of methylene chloride caused the formation of a ppt., which was collected and recrystallized from chloroform-methanol to give 6.0 g (70%) of off-white crystals, m.p. 188°–189° C.

Analysis: Calculated for $C_{19}H_{15}NO_5$: C, 67.65; H, 4.48; N, 4.15. Found: C, 67.91; H, 4.50; N, 4.20.

INTERMEDIATE 4

7-Benzoyl-1H-indole-3-propanoic acid

A 2.4 g (0.07 mole) sample of 2-[(7-benzoyl-1H-indol-3-yl)methyl]propanedioic acid was heated at 190° C. under vacuum until carbon dioxide evolution ceased (½ hr). The syrup was cooled to give 2.1 g (100%) of a yellow solid, m.p. 166.5°–168-5° C.

Analysis: Calculated for $C_{18}H_{15}NO_3$: C, 73.71; H, 5.16; N, 4.78. Found: C, 73.76; H, 5.11; N, 4.84.

INTERMEDIATE 5

(4-Chlorophenyl)-[3-[(dimethylamino)methyl]-1H-indol-7-yl]methanone

This compound was prepared by the procedure used to synthesize the compound of Intermediate 1. A combination of 13.5 g (0.12 mole) of 40% aqueous dimethylamine, 16.5 g (0.275 mole) of acetic acid, 9.3 g (0.115 mole) of 37% formalin, and 28.1 g (0.11 mole) of (4-chlorophenyl)(1H-indol-7-yl)methanone gave 35.3 g (99%) of crude title compound. Two recrystallizations of a small sample from 2-propanol gave white crystals, m.p. 95°–99° C.

Analysis: Calculated for $C_{18}H_{17}ClN_2O$: C, 69.12; H, 5.48; N, 8.96. Found: C, 69.27; H, 5.51; N, 8.82.

INTERMEDIATE 6

2-[[7-(4-Chlorobenzoyl)-1H-indol-3-yl]methyl]-propanedioic acid, diethyl ester

This compound was prepared by the procedure used to synthesize the compound of Intermediate 2, substituting dimethylsulfoxide to replace xylene as solvent. A combination of 4.2 g (0.1 mole) of 57% sodium hydride, 30 ml of dimethyl sulfoxide, 80 g (0.5 mole) of diethylmalonate and 31.2 g (0.1 mole) of (4-chlorophenyl)-[3-[(dimethylamino)methyl]-1H-indol-7-yl]methanone, gave 45 g of crude title compound. A small sample (3.1 g) was purified by HPLC to give, after a recrystallization from 90% aqueous ethanol, 2.0 g (67%) of yellow crystals, m.p. 102.0°–102.5° C.

Analysis: Calculated for $C_{23}H_{22}ClNO_5$: C, 64.56; H, 5.18; N, 3.27. Found: C, 64.71; H, 5.21; N, 3.38.

INTERMEDIATE 7

2-[[7-(4-Chlorobenzoyl)-1H-indol-3-yl]methyl]-propanedioic acid

This compound was prepared by the procedure used to synthesize the compound of Intermediate 3. A batch of 28.8 g (0.067 mole) of 2-[[7-(4-chlorobenzoyl)-1H-indol-3-yl]methyl]propanedioic acid diethyl ester and 600 ml of 3N sodium hydroxide gave, after a recrystallization from chloroform-methanol, 19.5 g (79%) of pale yellow crystals, m.p. 197°–201° C. with decomposition.

Analysis: Calculated for $C_{19}H_{14}ClNO_5$: C, 61.38; H, 3.80; N, 3.77. Found: C, 61.58; H, 3.81; N, 3.83.

INTERMEDIATE 8

7-(4-Chlorobenzoyl)-1H-indole-3-propanoic acid

This compound was prepared by the procedure used to synthesize the compound of Intermediate 4. A batch of 18.9 g (0.51 mole) of 2-[[7-(4-chlorobenzoyl)-1H-indol-3-yl]methyl]propanedioic acid heated to 200° C. gave 16.6 g (100%) of a dark yellow solid, m.p. 190°–202° C.

Analysis: Calculated for $C_{18}H_{14}ClNO_3$: C, 65.96; H, 4.31; N, 4.27. Found: C, 66.13; H, 4.25; N, 4.28.

EXAMPLE 1

2-Amino-3-benzoyl-γ-oxobenzenebutanoic acid

A solution of 8.7 g (0.03 mole) of 7-benzoyl-1H-indole-3-propanoic acid in 300 ml of ethyl acetate and 100 ml of abs. ethanol was ozonized until ozone was present above the solution. The yellow solution was then treated with 16.6 g (0.1 mole) of potassium iodide in 30 ml of acetic acid and 30 ml of water. After stirring 1 hr, the liberated iodine was removed by washing with a 15% sodium thiosulfate solution and the yellow organic layer was concentrated. The residue was dissolved in 100 ml of ethanol and 20 ml of 6N hydrochloric acid and heated at reflux for 16 hr. The dark red solution was concentrated and the residue was partitioned between dil. sodium hydroxide and methylene chloride. The basic aqueous layer was made acidic and the pH was adjusted to 2–3 by the addition of dil. sodium hydroxide. The solid was collected and dried, then recrystallized from benzene isopropyl ether to give 5.9 g (67%) of yellow powder, m.p. 161.0°–2.5° C.

Analysis: Calculated for $C_{17}H_{15}NO_4$: C, 68.68; H, 5.09; N, 4.71. Found: C, 68.82; H, 5.11; N, 4.67.

EXAMPLE 2

2-Amino-3-(4-chlorobenzoyl)-γ-oxobenzenebutanoic acid, ethyl ester

A solution of 13.1 g (0.04 mole) of 7-(4-chlorobenzoyl)-1H-indole-3-propanoic acid in 450 ml of ethyl acetate and 150 ml of absolute ethanol was treated with ozone until ozone was present above the solution. The solution was then stirred with an aqueous solution of potassium iodide, followed by a wash with aqueous sodium thiosulfate. The organic fraction was concentrated and the residue was dissolved in 250 ml of 190 proof ethanol. The solution was heated to reflux, 150 ml of 6N hydrochloric acid was added, and heating was continued for 18 hr. The mixture was diluted with 400 ml of water and a gummy solid separated. The gum was partitioned between dilute sodium hydroxide solution and methylene chloride. The basic aqueous fraction contained only a small amount of acidic material upon acidification, so it was discarded. The methylene chloride layer was dried over anhydrous sodium sulfate and passed through a column of silica gel. The yellow-colored eluant was concentrated and the crystalline residue was recrystallized from cyclohexane to give 3.5 g (26%) of bright yellow powder, m.p. 112°–115° C.

Analysis: Calculated for $C_{19}H_{18}ClNO_4$: C, 63.43; H, 5.04; N, 3.89. Found: C, 63.52; H, 5.04; N, 3.92.

EXAMPLE 3

2-Amino-3-(4-chlorobenzoyl)-γ-oxobenzenebutanoic acid

A solution of 3.3 g (0.0092 mole) of 2-amino-3-(4-chlorobenzoyl)-γ-oxobenzenebutanoic acid ethyl ester in 70 ml of hot 190 proof ethanol was treated with 40 ml of 4N aqueous sodium hydroxide solution and the mixture was heated at reflux for 18 hr. The hot mixture was filtered and the insoluble material was discarded. The filtrate was cooled and the precipitate collected by filtration. This precipitate was partitioned between dilute hydrochloric acid and methylene chloride. The organic layer was separated, dried over magnesium sulfate and concentrated to give 2.7 g (89%) of bright yellow crystals, m.p. 172°–177° C.

Analysis: Calculated for $C_{17}H_{14}ClNO_4$: C, 61.55; H, 4.25; N, 4.22. Found: C, 61.43; H, 4.24; N, 4.24.

PHARMACOLOGY

Acute Anti-inflammatory Test—Evans Blue-Carrageenen Pleural Effusion Assay

The method is that of Sancilio and Fishman in TOXICOL. APPL. PHARMAC. 26, 575–584 (1973). Fasted Sprague-Dawley male rats, weighing between 250–500 g were randomly divided into control and experimental groups of six animals one hour after oral administration of the compounds, e.g., Formula I compounds or indomethacin, the rats were etherized and 5 ml of a mild irritant solution (0.075% Evans blue and 0.5% carrageenan type 7) was administered intrapleurally. Five hours later, the animals were sacrificed with carbon dioxide, pleural fluids were collected in calibrated centrifuge tubes and measured. Results were expressed as the average percent decrease in volume of pleural fluid from that of the control group. The carrier was 0.5% Tween 80 in distilled water and was also the control article. Potency as compared to indomethacin was determined by regressional analysis by the method of Bliss, C. (1951) VITAMIN METHODS VOL. 2, pp 445-610, Ed. by Gyorgy, N. Y. Academic Press. Using this procedure, it was determined that the compound of Example 1 was 1.73 (0.78-3.62) times the potency of indomethacin or considering the overlap of confidence limits, it is about as potent as indomethacin in the foregoing pleural effusion anti-inflammatory assay over the range of 0.16 to 4.0 mg/kg body weight.

Chronic Anti-inflammatory Test-Adjuvant-Induced Arthritis Assay

A modification of the method of Walz et al, J. PHARMAC. EXP. THER. 178, pp 223-31 (1971), was used. This consisted of a therapeutic rather than a prophylactic dosing regimen.

Female Lewis Wistar rats, weighing between 150 and 235 g, were used. On day 0 a tattoo was made on each leg at the point where the Achilles tendon enters the gastrocnemius muscle. This served as a reference point for measuring the limb volume, plethysmographically. Several hours later, 0.05 ml of a suspension of 1.5% *Mycobacterium butyricum* in mineral oil was injected into the subplantar surface of the right hind foot. On day 18 the hind limb volumes of both feet were determined. Animals with significant swelling of the uninjected feet were randomized by block design into groups of seven or eight. They were dosed orally five days/week, starting on day 18, with the last dose being given on day 28. Twenty-four hours after the last dose, the edema of the injected and uninjected feet was determined by difference. Results were expressed as milliliter of edema of the injected and uninjected feet.

In this test, the compound of Example 3 was found to be 0.86 (0.47-1.7) times as potent as indomethacin.

Analgesia Test—Acetylcholine-induced Abdominal Constriction in Mice

The method is a modification of that of Collier, H. O. J. et al., J. BR. PHARMAC. CHEMOTHER. 32, 295-310 (1968). Fed female mice are randomized into groups of 10. Group 1 received the control article (carrier) which was 0.5% Tween 80 in distilled water (10 ml/kg). Test agent was suspended in 10 ml/kg of the carrier and administered by gavage to the mice and 180 min later acetylcholine bromide in 0.06% saline was administered intraperitoneally. Immediately thereafter, each mouse was placed under an inverted 1-liter beaker and observed for 3 min for the presence of abdominal constriction. The compound of Example 3 prevented abdominal constriction in 70% of the mice when administered at 4.0 mg/kg in 10 ml/kg of the carrier. This compared to 60% blocked by 1.0 mg/kg indomethacin under the same conditions.

Formulation and Administration

The present invention also contemplates novel therapeutic compositions containing the compounds of the invention as active ingredients. Effective quantities of any of the foregoing pharmacologically active compounds may be administered to a living animal body in any one of various ways; for example, orally as in capsules or tablets, parenterally in the form of sterile solutions or suspensions, and in some cases intravenously in the form of sterile solutions. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerine, glucose syrup and the like.

The pharmacologically active compounds may be advantageously employed in a unit dosage of from 0.1 to 250 milligrams or more depending on the size of the animal. For example, a large animal such as a horse may require tablets of 500-1000 milligrams active ingredient. The unit dosage may be given a suitable number of times daily so that the daily dosage may vary from 0.3 to 450 milligrams. Five to 25 milligrams appears optimum per unit dose.

It is only necessary that the active ingredient constitute an effective amount, i.e., such that a suitable effective dosage will be obtained consistent with the dosage form employed. The exact individual dosages as well as daily dosages will, of course, be determined according to standard medical principles under the direction of a physician or veterinarian.

The active agents of the invention may be combined with other pharmacologically active agents, or with buffers, antacids or the like, for administration and the proportion of the active agent in the compositions may be varied widely.

The following are examples of compositions formed in accordance with this invention.

1. Capsules

Capsules of 5 mg., 25 mg., and 50 mg. of active ingredient per capsule are prepared. With the higher amounts of active ingredient, adjustment may be made in the amount of lactose.

| Typical blend for encapsulation | Per capsule, mg. |
|---|---|
| Active ingredient | 5.0 |
| Lactose | 296.7 |
| Starch | 129.0 |
| Magnesium stearate | 4.3 |
| Total | 435.0 mg. |

Additional capsule formulations preferably contain a higher dosage of active ingredient and are as follows.

| Ingredients | Per capsule, mg. |
|---|---|
| Active ingredient | 25.0 |
| Lactose | 306.5 |
| Starch | 99.2 |
| Magnesium stearate | 4.3 |
| Total | 435.0 mg. |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

| | Per tablet, mg. |
|---|---|
| (1) Active ingredient | 5.0 |
| (2) Corn starch | 13.6 |
| (3) Corn starch (paste) | 3.4 |
| (4) Lactose | 79.2 |
| (5) Dicalcium phosphate | 68.0 |
| (6) Calcium stearate | 0.9 |
| | 170.1 mg. |

Uniformly blend 1, 2, 4, and 5. Prepare 3 as a 10 percent paste in water. Granulate the blend with starch paste and pass the wet mass through an eight mesh screen. The wet granulation is dried and sized through a twelve mesh screen. The dried granules are blended with the calcium stearate and pressed.

3. Injectable—2% sterile solutions

| | Per cc. |
|---|---|
| Active ingredient | 20 mg. |
| Preservative, e.g., chlorobutanol | 0.5% weight/volume |
| Water for injection | q.s. |

Prepare solution, clarify by filtration, fill into vials, seal and autoclave.

Various modifications and equivalents will be apparent to one skilled in the art and may be made in the compounds, compositions, and methods of the present invention without departing from the spirit or scope thereof, and it is therefore understood that the invention is to be limited only by the scope of the appended claims.

What is claimed is:

1. A compound selected from the group having the formula:

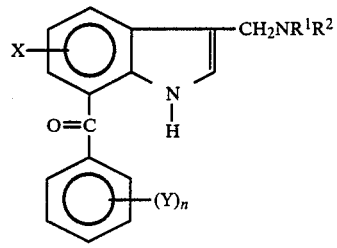

wherein;

X is selected from hydrogen, halogen, or loweralkyl;
Y is selected from hydrogen, halogen, loweralkyl, nitro, trifluoromethyl, or loweralkoxy;
n is 1 or 2; and
$R^1$ and $R^2$ are selected from loweralkyl, or when taken together with the adjacent nitrogen atom, may form a heterocyclic amine selected from 1-pyrrolidinyl, 1-piperidinyl, or 4-morpholinyl.

2. The compound of claim 1 which is [3-[(dimethylamino)methyl]-1H-indol-7-yl]phenylmethanone.

3. The compound of claim 1 which is (4-chlorophenyl)-[3-[(dimethylamino)methyl]-1H-indol-7-yl]methanone.

* * * * *